(12) United States Patent
Pots et al.

(10) Patent No.: US 7,104,147 B2
(45) Date of Patent: Sep. 12, 2006

(54) SYSTEM AND METHOD FOR MEASURING ELECTRIC CURRENT IN A PIPELINE

(75) Inventors: Bert Pots, Houston, TX (US); Kola Fagbayi, Houston, TX (US); P. Kevin Scott, Harvey, LA (US); Mark W. Mateer, Katy, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/768,618

(22) Filed: Jan. 30, 2004

(65) Prior Publication Data

US 2005/0168208 A1    Aug. 4, 2005

(51) Int. Cl.
*G01M 19/00* (2006.01)
*G01R 27/08* (2006.01)
*G01R 19/155* (2006.01)

(52) U.S. Cl. ............ 73/865.8; 324/716; 324/718
(58) Field of Classification Search ............ 324/700, 324/716, 718, 72, 72.5, 149; 73/865.8, 865.9, 73/866.5, 86, 104, 152.54, 152.57, 431, 865
See application file for complete search history.

(56) References Cited

U.S. PATENT DOCUMENTS

| | | | | |
|---|---|---|---|---|
| 2,190,320 A | * | 2/1940 | Potapenko | 324/362 |
| 2,475,680 A | * | 7/1949 | Sorensen | 324/552 |
| 2,980,854 A | | 4/1961 | Dean et al. | 324/72 |
| 3,460,028 A | * | 8/1969 | Beaver et al. | 324/220 |
| 3,539,915 A | * | 11/1970 | Wood et al. | 324/220 |
| 3,568,053 A | * | 3/1971 | Kilpatrick et al. | 324/722 |
| 4,427,943 A | * | 1/1984 | Cloutier et al. | 324/326 |
| 4,639,677 A | | 1/1987 | Goolsby | 205/730 |
| 4,654,702 A | * | 3/1987 | Tolino et al. | 348/84 |

(Continued)

FOREIGN PATENT DOCUMENTS

EP    0 235 478 B1    11/1993

OTHER PUBLICATIONS

"Application of Cathodic Protection for External Surfaces of Steel Well Casings," Reaffirmed Sep. 20, 2001, pp. 1-25, NACE Standard Recommended Practice, RP0186-2001, Item No. 21031, NACE International, Houston, Texas.

(Continued)

*Primary Examiner*—Daniel S. Larkin
*Assistant Examiner*—David A. Rogers
(74) *Attorney, Agent, or Firm*—William E. Hickman (57) ABSTRACT

A system and method for measuring a voltage differential in a current-carrying pipe using a propulsion vehicle. The system may be adapted for use with a pipeline pig or other propulsion device, which is configured to determine the electric current in a pipeline with nominal noise while the apparatus is moving. One aspect of the present invention is a pig which is outfitted with electrical contacts. These electrical contacts may optionally consist of rotating steel brushes and/or rotating steel knives. The pig includes data logging capabilities which may record location and voltage data. A pig according to the present invention optionally may include electromechanical devices which reduce electrical noise.

48 Claims, 6 Drawing Sheets

U.S. PATENT DOCUMENTS

| | | | |
|---|---|---|---|
| 4,742,298 A * | 5/1988 | Ando et al. | 324/220 |
| 4,804,906 A * | 2/1989 | Hamberg et al. | 324/718 |
| 4,857,831 A | 8/1989 | Davies et al. | 324/65 |
| 5,426,367 A * | 6/1995 | Martin et al. | 324/339 |
| 5,565,633 A * | 10/1996 | Wernicke | 73/865.8 |
| 5,717,334 A * | 2/1998 | Vail et al. | 324/368 |
| 5,747,998 A * | 5/1998 | Fowler et al. | 324/263 |
| 6,031,381 A * | 2/2000 | Vail et al. | 324/716 |
| 6,066,034 A | 5/2000 | Hettes et al. | 451/466 |
| 6,359,434 B1 * | 3/2002 | Winslow et al. | 324/220 |
| 6,474,165 B1 | 11/2002 | Harper et al. | 73/623 |
| 6,489,771 B1 | 12/2002 | Farque | 324/326 |
| 6,538,431 B1 * | 3/2003 | Couchman et al. | 324/220 |
| 6,553,322 B1 * | 4/2003 | Ignagni | 702/34 |
| 6,680,619 B1 * | 1/2004 | Horn | 324/700 |
| 2001/0029989 A1 | 10/2001 | Paz | 138/104 |
| 2002/0196160 A1 | 12/2002 | Hilleary | 340/870.16 |
| 2003/0074162 A1 | 4/2003 | Fourie et al. | 702/188 |
| 2003/0121338 A1 | 7/2003 | Yates | 73/865.8 |
| 2003/0189435 A1 | 10/2003 | Yunovich et al. | 324/700 |
| 2003/0198374 A1 | 10/2003 | Hagene et al. | 382/141 |
| 2004/0189289 A1 * | 9/2004 | Atherton | 324/220 |

OTHER PUBLICATIONS

Robert Elmer, "Cogeneration Plant Uses 'Smart Pigs' to Help Ensure Pipeline Safety," Nov. 2003, pp. 18-20, *NACE International Materials Performance* Periodical.

"CPET Corrosion Protection Evaluation Service," Nov. 3, 2003, p. 1, Schlumberger website http://www.slb.com.

R. Kelso Riddell, "Subsea Pipeline Pig Tracking," first published in Dec. 1986, revised Jul. 1998, pp. 1-19, *PIGMAN98*, Oceano Instruments (UK) Ltd., Granton, Edinburgh, Scotland.

"Remote Pig Signalling System," undated, pp. 1-2, printed from Online Electronics Ltd. website, www.online-electronics.com, Product Ranges, Other Systems, datasheet OELremote_signaling.pdf.

"StarTrak Pigging Satellite Monitoring Systems," undated, 4 pages, printed from StarTrak Pigging Technologies, Inc. website, www.starpig.com, Products, Satellite Monitoring Systems.

Search Report dated Apr. 27, 2005.

* cited by examiner

SYSTEM AND METHOD FOR MEASURING ELECTRIC CURRENT IN A PIPELINE

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates to cathodic protection systems for corrosion protection of metal objects which are buried in soil or located underwater. More particularly, the present invention relates to a system and method for measuring the electric current in a pipeline imposed by a cathodic protection system.

BACKGROUND OF THE INVENTION

The owners of pipelines frequently wish to monitor the status or condition of a pipeline or to check the integrity of a protection system. This may include measurement of the material type, internal diameter, and thickness of the pipe, the material type, and thickness of any internal lining if present, the presence of corrosion on the pipe, damage to the lining, the thickness of any deposits of material on the internal surface of the pipe or of the lining if present, the presence and extent of circumferential cracks, the presence and extent of longitudinal cracks, and the position of features such as bends, offtakes, valves and joints. In view of the high cost of replacing pipe, and the potential consequential damage due to fluid loss from a break in the pipe, it is justifiable to carry out regular surveys of the condition of the pipe from within the pipe using a vehicle transported inside the pipe. Such vehicles are well known in the art and are often referred to as a smart or intelligent pig, hereinafter simply referred to as "pig".

Pigs may be outfitted with electronic instruments designed to inspect pipelines internally and may physically travel with a fluid product within the pipelines without simultaneously interrupting fluid flow. As will be appreciated by those skilled in the art, a pig may detect various pipeline defects. Furthermore, due to pipelines being situated on, in, or under a diversity of terrains throughout the world, pigs are capable of traveling within multi-diameter pipelines and bends therein and are capable of detecting the location of pipe-related problems. Those skilled in the art will recognize that a wide variety of data logging devices on board pigs are well known in the art. Depending on the technology and degree of sophistication used by a pig, its sensors will record the distance traveled, location and position of features and defects, and the depth and magnitude thereof. Pigs are frequently used inside pipelines to detect the presence of corrosion and other defects.

To prevent pipe external corrosion, a cathodic protection (CP) system may be implemented. CP is a method of combating corrosion of metals that come in contact with potentially corrosive mediums. The purpose of cathodic protection is to reduce or eliminate corrosion of steel or other metals in a given environment. The corrosion of metal in an electrolyte at ambient temperature is an electrochemical process involving the flow of electrons in metals and ions in electrolytes. This corrosion can be controlled by the application of currents from an external source such as a generator or rectifier, or from a galvanic sacrificial anode, which supplies all of the current for the electrochemical reduction of the corrodant by a source other than the corroding steel. If all of the current for the electrochemical reduction is supplied by the external source, the corrosion of the steel is reduced.

There are two widely used systems for generating opposing electrical currents, "sacrificial systems" and "impressed current systems." In sacrificial systems, the current is supplied by another metal which is galvanically more reactive than the metal of the structure. For example, metals such as aluminum, magnesium and zinc are galvanically more active than steel and are used as "sacrificial anodes" to protect steel structures. In impressed current systems, a non-consumable metal is used to drain direct current (DC) supplied from an external source into the electrolyte, which passes to the structure to be protected. The parts from which the current is drained are called "anodes" and the protected structure is called a "cathode." In both sacrificial and impressed current systems of cathodic protection, a path between the anode and the cathode is essential for flow of current to protect the structure.

In order to ensure that a CP system is properly protecting a pipeline, the prior art teaches a variety of methods for monitoring the potential difference in a pipeline imposed by the system. One such method involves installing a standard reference electrode at one or more locations along the pipeline together with a conductor connected to the pipeline. A technician periodically visits the location and measures the voltage between the standard reference electrode and the pipeline using a voltmeter. A responsible person then examines the collected data looking for inadequate voltages and variations from earlier data and, when control is inadequate or excessive, adjusts the output(s) of the appropriate rectifier(s). Such a method is limited in that only current at static locations is measured and a technician is required to visit such locations.

Another commonly used potential survey method is the close interval survey in which the pipe-to-medium potential is recorded as a function of distance along the pipeline of interest. Any potentials which departed significantly from the potentials at other regions or which deviated significantly from prior surveys, could be identified as possible stray current pickup or discharge points. This method involves pipeline maintenance personnel traveling to the pipeline and making the measurements described above. Single location, time-dependent surveys are also performed by the maintenance staff by monitoring the potential at a chosen location as a function of time. Any significant changes in the recorded potentials could indicate possible intermittent pickup or discharge of stray current. This technique also provides only static data and is labor intensive In yet another prior art embodiment, a downhole apparatus with a plurality of electrodes is lowered into a casing. Examples of this embodiment are given in Davies, et al., U.S. Pat. No. 4,857,831, and NACE International Standard RPO186-2001 at Appendix A. The downhole apparatus is suspended by a long cable which is connected to a measurement unit located at the ground surface, and potential difference measurements are taken by the measurement unit at the ground surface as the downhole apparatus traverses the length of the casing. Since the potential difference information must be transmitted to the measurement unit at the ground surface through the long cable connecting the downhole apparatus to the measurement unit, the information tends to be degraded due to noise pick-up and crosstalk. In addition, thermal effects along the long cable and at the electrical connections on the surface and in the downhole tool adversely affect the information. The electrodes utilized in this embodiment are not configured for dynamic electrical contact with the pipe, and, if such dynamic contact were attempted, the signal would be unacceptable due to noise distortion.

Accordingly, there is a need for improved system for monitoring electrical current imposed by a cathodic protection system over a continuum using a pig or similar vehicle for propulsion. The system should be able to dynamically and efficiently measure the voltage difference between points in a pipeline, while minimizing noise and deviations caused by thermal effects.

SUMMARY OF THE INVENTION

The present invention meets the above needs and overcomes one or more deficiencies in the prior art by providing a system using a propulsion vehicle that is configured to measure a voltage differential in a current-carrying pipe. The propulsion vehicle may be outfitted with two contacts for maintaining electrical contact with the pipe as the vehicle moves through the pipe. These electrical contacts may optionally include rotating steel brushes and/or rotating steel knives. The system further includes a voltage-reading device connected to the contacts for measuring the voltage between the contacts as the vehicle moves through the pipe. A vehicle according to the present invention optionally may include electromechanical devices that reduce electrical noise.

According to another aspect of the present invention, a method is provided for measuring a voltage differential in a current-carrying pipe. A propulsion vehicle having two or more contacts is inserted into a pipe. The contacts are utilized to make electrical contact with the pipe, and the voltage between the contacts is determined as the vehicle moves through the pipe. The vehicle may optionally output voltage and/or position data.

Other objects, features, and advantages of the invention will become apparent to those skilled in the art upon reference to the following detailed description of the invention and the accompanying drawings.

BRIEF DESCRIPTION OF THE DRAWINGS

The present invention is described in detail below with reference to the attached drawing figures, wherein like numbers denote like parts throughout the several views.

DETAILED DESCRIPTION OF THE INVENTION

The present invention provides a system and method for measuring the electric current in a pipeline imposed by a cathodic protection system. To accomplish this, a pig is utilized.

Pigs are well known in the art and are frequently used inside pipelines to detect the presence of corrosion and other defects. Pigs may be outfitted with electronic instruments designed to inspect pipelines internally and may physically travel with a fluid product within the pipelines without simultaneously interrupting fluid flow.

Those skilled in the art will recognize a variety of techniques exist for tracking the location of a pipeline pig. In general, odometers have historically been used for distance/location tracking of pigs. Odometer technology has continued to improve over time with the incorporation of onboard electronic instrumentation. Other technologies have also been developed to track a pig's location in real-time using satellite (i.e., GPS), subsea acoustic and other techniques for various applications. These techniques include, without limitation, Geiger counters, magnetics, radio, acoustics, pinger-based, and transponder-based systems. Those skilled in the art will recognize that any number of location tracking/logging techniques may be utilized with the present invention.

Figure 1:
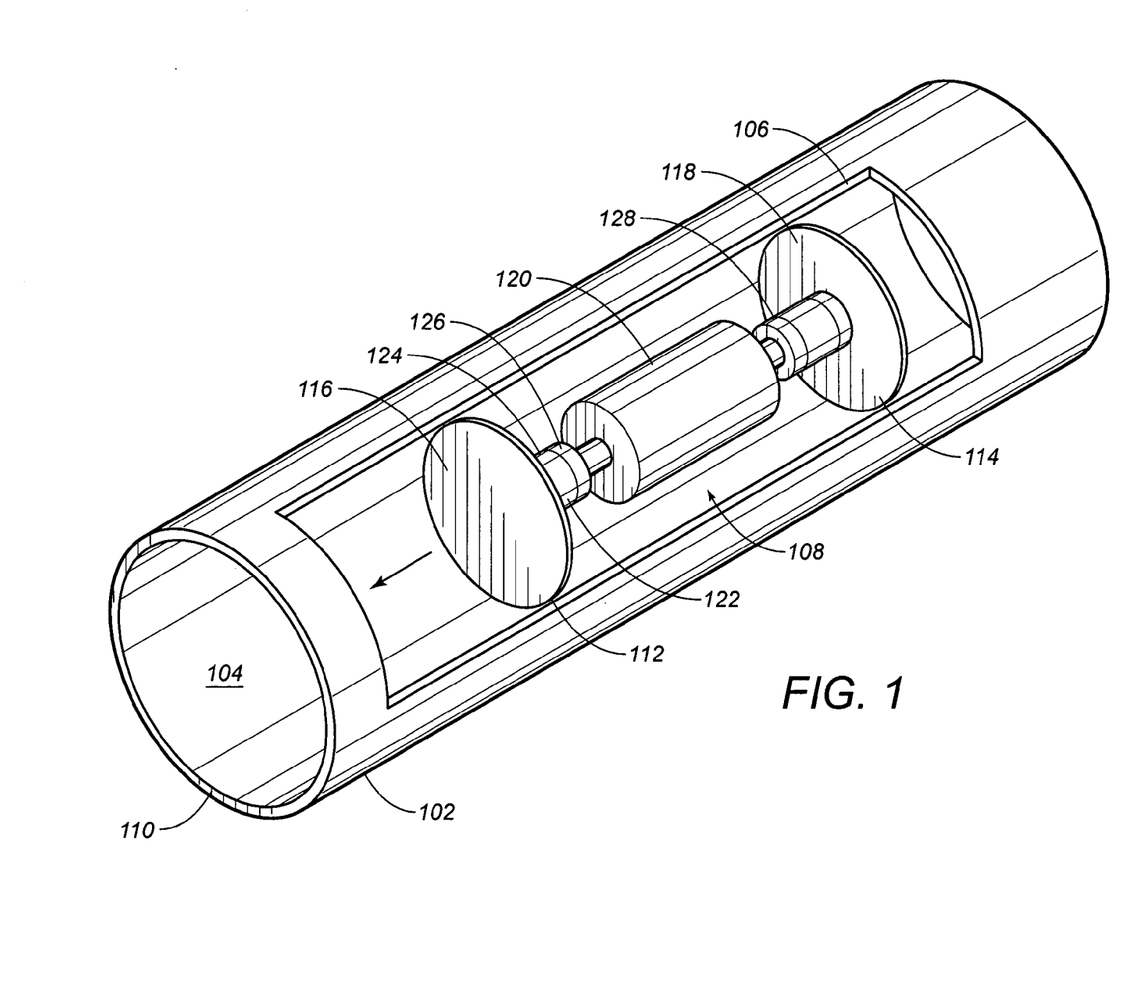
FIG. 1 is a cut-away section of a pipe illustrating a schematic view of the present invention.

FIG. 1 shows a schematic view of a pipe 102 filled with a fluid 104. A cut-away section 106 shows a pig 108 according to the present invention. As will be understood by those of skill in the art, the fluid 104 may propel the pig 108 through the pipe 102. The pig 108 is in electrical contact with the internal pipeline wall 110 at electrically separated contact locations 112 and 114. It is preferable for locations 112 and 114 to have multiple points of contact with the wall 110. Such electrical contact with the wall 110 is achieved by contacts 116 and 118, which are arranged in a spaced apart relationship upon the pig 108 and which are connected to the pig body 120. The pig body 120 further includes a voltmeter device which has leads connected to contacts 116 and 118. Such a voltmeter is well known in the art and is capable of measuring the voltage differential between locations 112 and 114. Pig body 120 also may include a battery, an odometer, and data-logging device, which are commercially available and well known in the art. For example, voltage and location data may be logged by the pig 108. While the embodiment shown in FIG. 1 displays two contacts attached to a single pig, those skilled in the art will recognize that a plurality of connected pigs are acceptable use with the present invention. For example, a first pig may have a single contact, while a second pig provides the other needed contact.

An objective of the instant invention is to reduce noise resulting, in part, from the pig's movement and the invention contemplates a variety of techniques to reduce this noise. In various embodiments of the present invention, contacts 116 and 118 include rotating steel brushes and/or rotating steel knives. The brushes and knives may be utilized in various combinations to maintain electrical contact with the internal surface of the pipe 102 and, optionally, cleaning the internal surface of the pipe 102. For example, steel brushes sold by the Weiler Corporation (Item #08047) have been used to ensure good electrical contact. A combination of three brushes and three knives for each contact may be preferable for use with the present invention to reduce noise as the contacts 116 and 118 move through the pipe 102 and rotate in the direction indicated.

To further reduce noise, the present invention contemplates using electromechanical devices connected to the brush and/or knife contacts 116 and 118. In one embodiment, noise from these rotating components is reduced by using low-noise rotating electromechanical devices, such as mercury contacts and/or slip-ring contacts. Mercury contacts sold by Mercotac Inc. (Model number 110) have been used to successfully reduce noise to the microvolt range, while slip rings sold by Airflyte Electronics Company (Model #2400096-002) have been successfully used to transmit low noise signals. Those skilled in the art will recognize that any number of contact devices and/or low-noise electromechanical devices may be used with the current invention. In FIG. 1, for example, pig 108 includes electromechanical devices 122 and 128. As will be understood by those skilled in the art, device 122 includes a static element 126 and a dynamic element 124 which rotates along with the contact 116 to transmit the signal to the static element 126.

Figure 2:
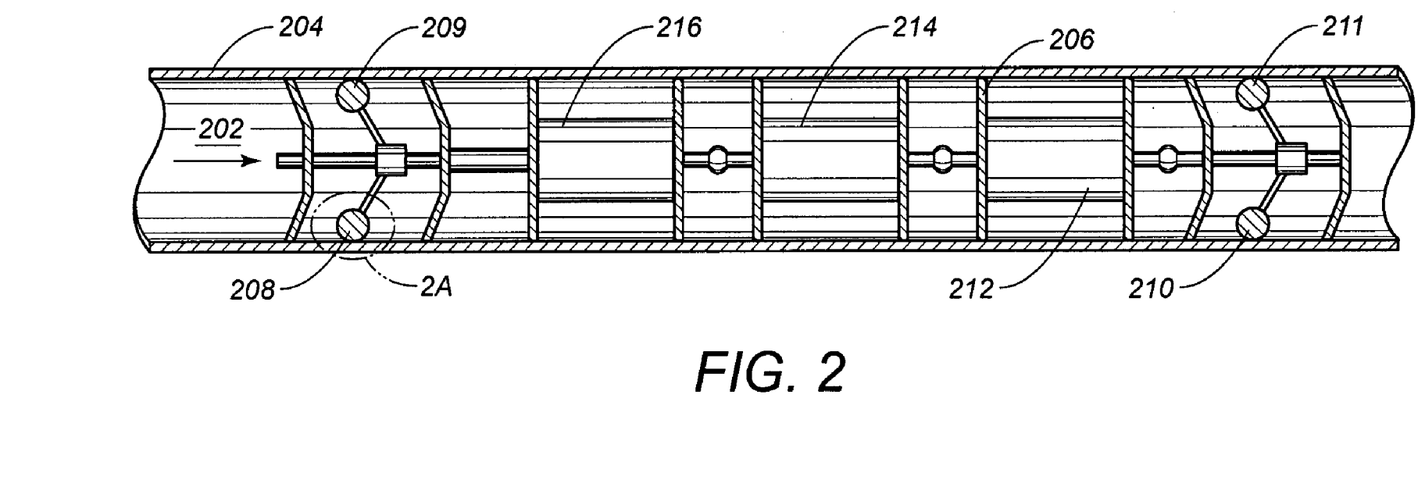
FIG. 2 is a cross section of a pipe illustrating a schematic view of another embodiment of the present invention.

FIG. 2 shows a pig 206 according to another embodiment of the present invention. The pig 206 is shown within a pipe 204, along with the fluid 202, which may propel the pig 206 in the direction indicated. The pig 206 is in electrical contact with the pipe 204 at electrically separated contact locations 208, 209, 210, and 211. It is only necessary, however, to implement two points of contact separated by a distance, such as points of contact 208 and 210. Such electrical contact is achieved by the contacts being mounted in a spaced apart relationship upon the pig 206. As discussed above, contacts 208, 209, 210, and 211 may include rotating steel brushes and/or rotating steel knives. For example a combination of three brushes and three knives may be utilized with the current invention. The contacts 208, 209, 210, and 211 may further include electromechanical devices. The pig 206 further includes a battery 216, a data logger 214, a voltmeter 212, and an embodiment of an odometer. These components are commercially available and well known in the art.

Figure 2A:
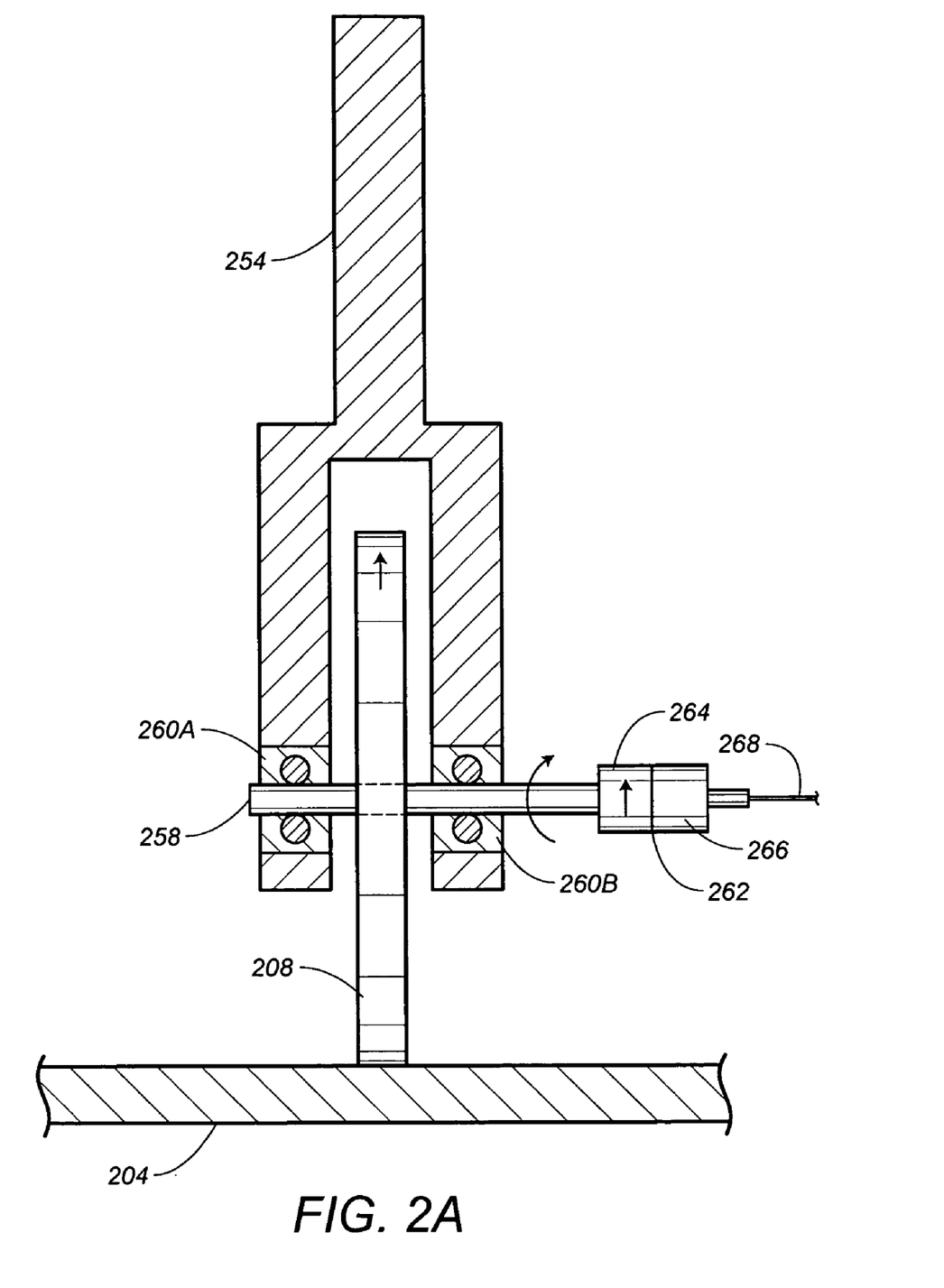
FIG. 2A is a schematic view of the electrical contact 2A in FIG. 2.

FIG. 2A illustrates the electrical contact 208. As discussed above, rotating, electrical contact 208 is utilized for electrical communication with the internal pipe wall 204. A connecting arm 254 serves to connect the contact 208 to the pig. An axel 258 runs through the arm 254 and connects the contact 208 to the pig while allowing the contact 208 to rotate in the direction indicated. The axel 258 rotates along with the contact 208 and such rotation is facilitated by ball bearing sets 260A and 260B. The axel 258 is in communication with an electromechanical device 262. As will be appreciated by those skilled in the art, the electromechanical device 262 includes a dynamic element 264, which rotates with the axel 258 and transmits the signal to a static element 266. An electrical wire 268 emerges from the device 262. The wire 268 may be connected to voltmeter 212. As will be understood by those of skill in the art, to measure the voltage differential between two contacts (208 and 210) on a pipe, the voltmeter 212 may receive a second wire that is connected to electrical contact 210 in the manner here described.

Figure 3:
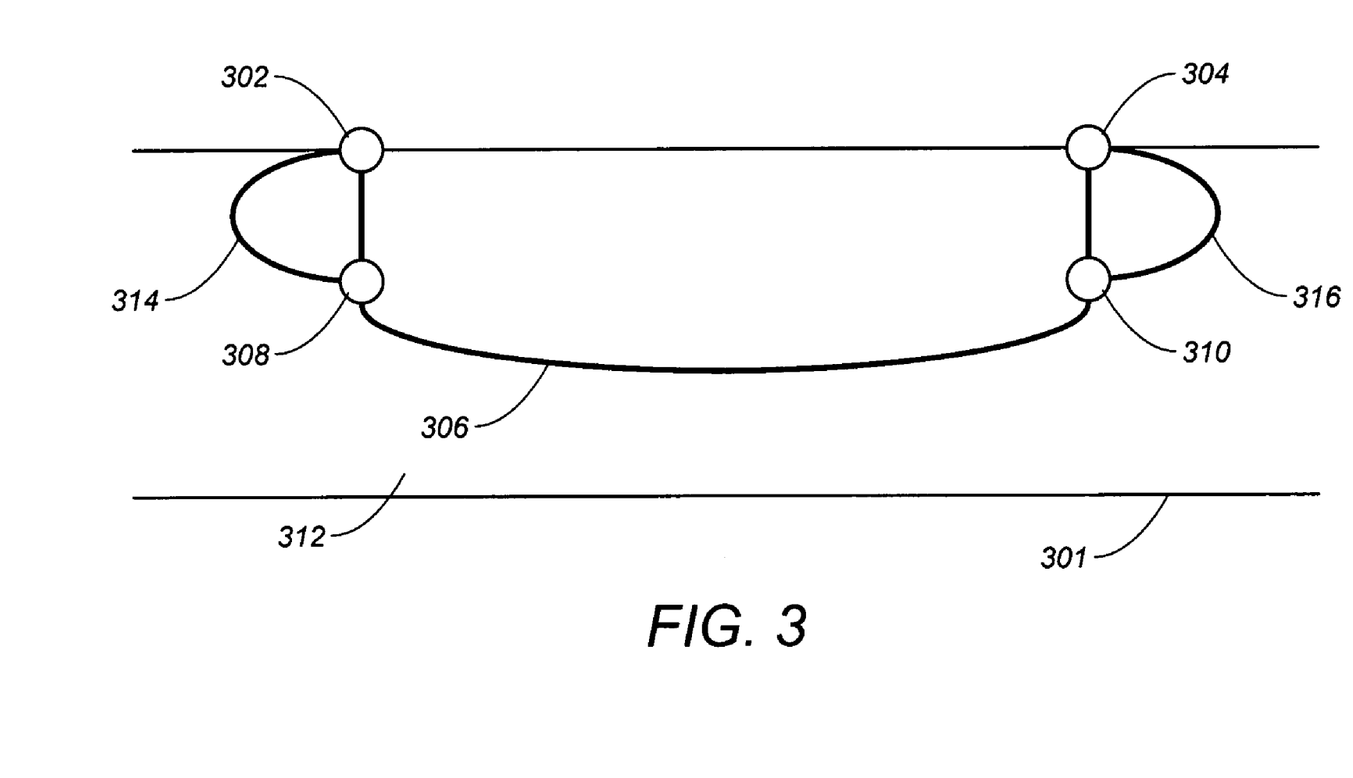
FIG. 3 is a temperature compensation system according to one embodiment of the present invention.

The present invention also contemplates compensating for thermocouple voltages that result from temperature effects. FIG. 3 shows a temperature compensation system according to one embodiment of the present invention. Because of potential temperature gradients along the pipeline wall, a thermocouple voltage may be experienced, which needs to be compensated for. However, the bulk fluid temperature will be stable, and, by measuring the thermocouple voltage difference between the pipeline wall at the electrical contact position and the bulk fluid, compensation can be made for temperature differences in the system. Different materials have to be used for the rolling contact devices with the wall in order to measure the temperature gradient for the compensation.

As shown in FIG. 3, points 302 and 304 reside upon the internal wall of a pipe. Such points may have different temperatures. The potential difference between the point 302 and the point 304 is the potential difference of interest and may be measured via a connection 306. The reference points 308 and 310 reside within the bulk fluid 312 and are not affected by temperature deviations. Connection 314 allows the potential difference between the contact point 302 and the bulk fluid reference point 308 to be measured. Connection 316 allows the potential difference between the contact point 304 and bulk fluid reference point 310 to be measured. Because of potential temperature differences at the pipe wall, thermocouple effects induce some of the voltage measured at the contacts. By measuring the voltage differences between the contacts and the references, these effects can be compensated for and the true potential difference between points 302 and 304 can be calculated.

The accuracy of the pig's data may also be adversely affected by no-contact events. No-contact events refer to an event in which the electrical contact between the pig and pipeline is interrupted. Those skilled in the art will recognize that no-contact events result in undesirable open-circuit signals. To detect no-contact events, the present invention may include an alternating current (AC) pilot signal to flag and exclude no-contact signals during data processing. For example, if a 1–10 kHz AC voltage source of 1 mV is incorporated into the electrical circuitry, a band-pass filter at the frequency of the source filters the pilot signal out. When the signal is present, there must be contact, while no signal indicates no contact. The use of an AC pilot signal is provided as an example, and those skilled in the art will recognize that a variety of techniques may be acceptable to flag no contact events.

Figure 4:
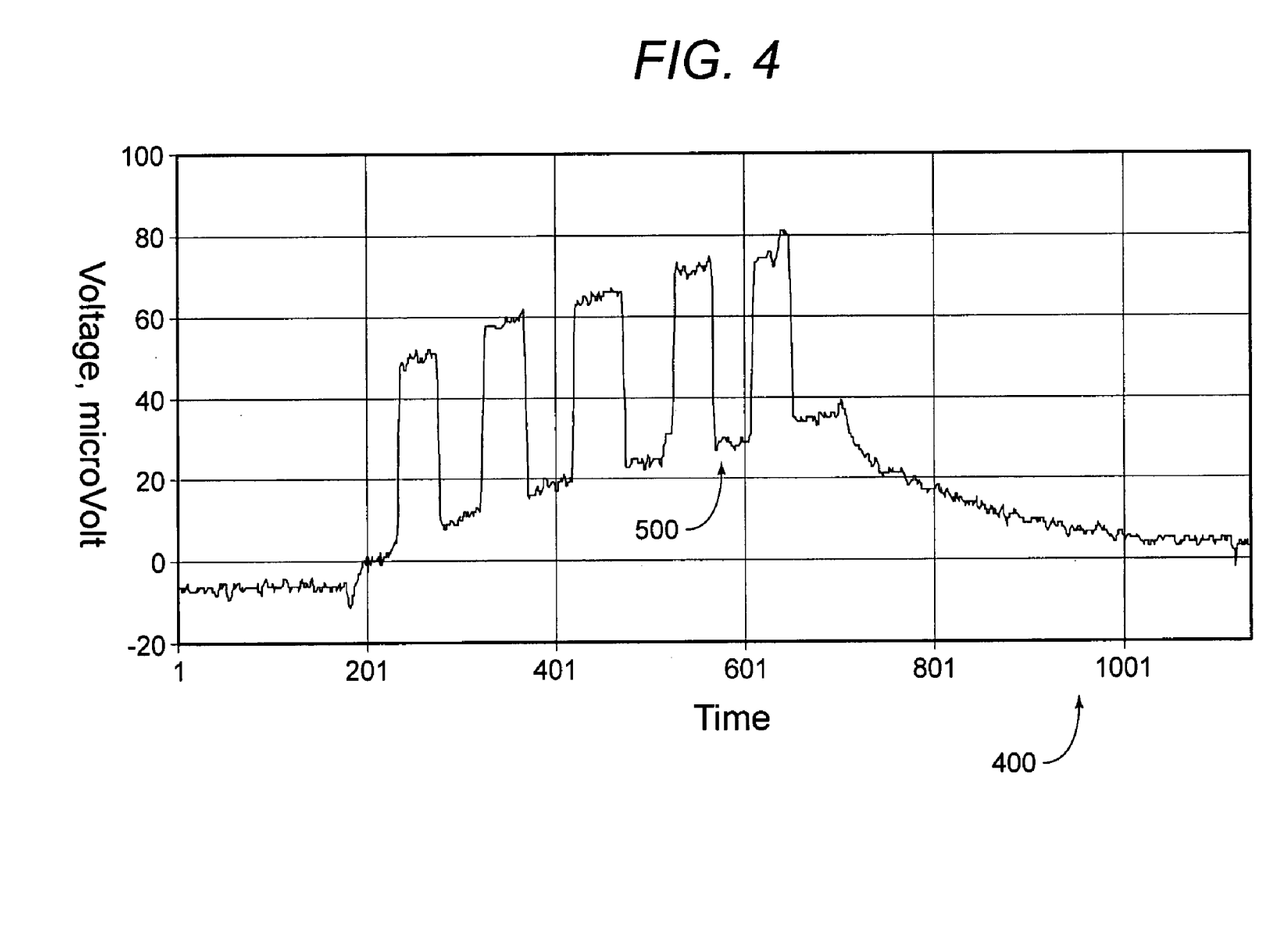
FIGS. 4 and 5 are exemplary test results obtained from a laboratory arrangement contemplating one embodiment of the present invention.
Figure 5:
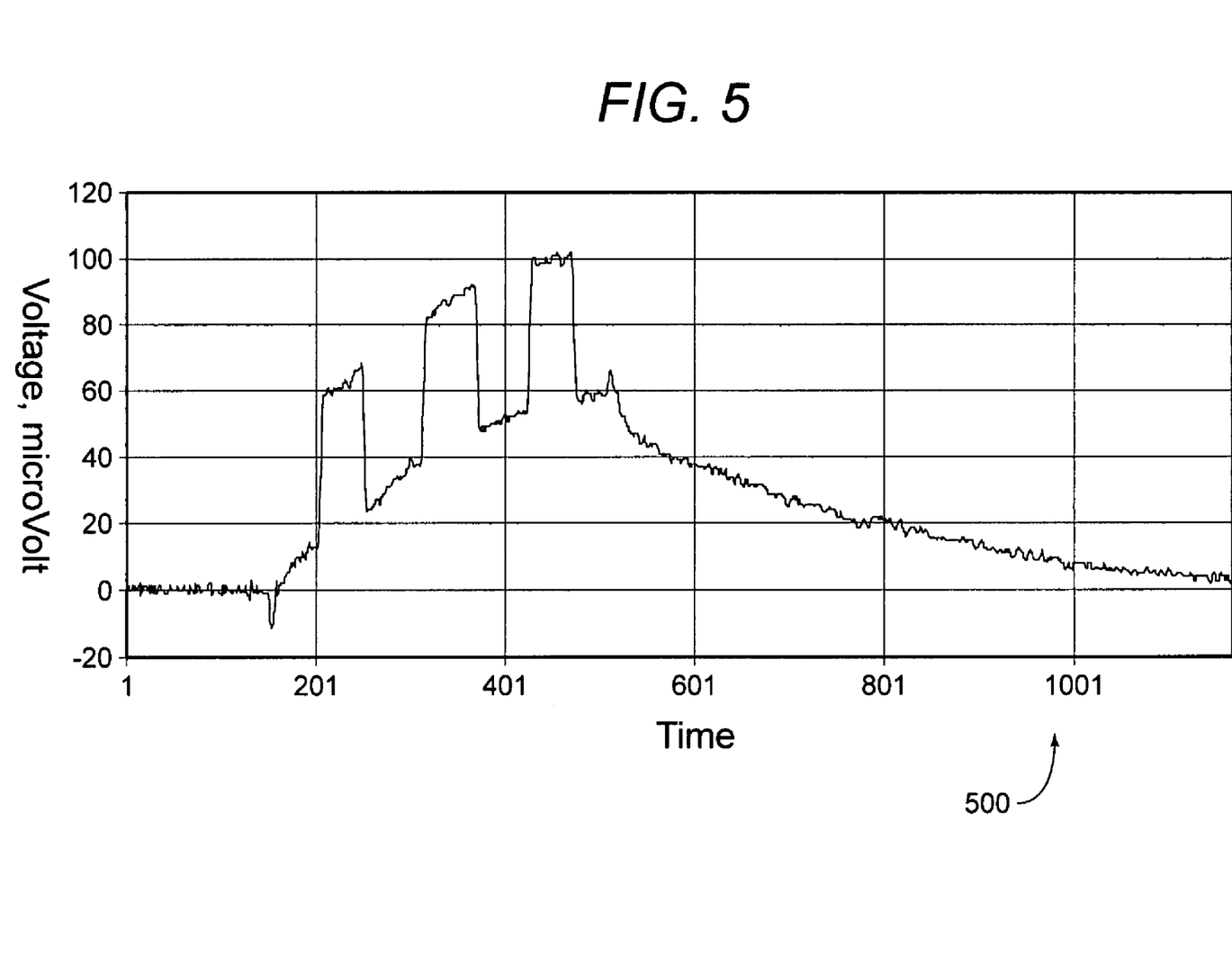

A variety of laboratory tests have demonstrated the performance of the present invention, and FIGS. 4 and 5 display exemplary test results. An artificial on-off voltage of 40 microvolt was incorporated into the electric circuit to see whether the intermittent voltage could be retrieved. The signal was successfully retrieved in each test. In FIG. 4, the speed of the rolling, rotating contacts was approximately 1.1 meters per second. Graph 400 displays exemplary results of this test. As shown in the graph 400, moderate baseline drift was experienced by the output. Thermo-effects, for which no compensation was made, caused this drift. FIG. 5 displays results of the same test, except that the speed of the rolling, rotating contacts was approximately 2 meters per second, which is on the high side of typical velocities seen in transportation of liquids. Graph 500 displays exemplary results of this test. Slightly greater base line drift was experienced because the increased speed of the contacts produced greater thermal dynamic effects, for which no compensation was attempted.

As a result of these and additional tests, it has been shown that a pig according to the present invention can successfully measure the electric current in a pipeline imposed by a cathodic protection system. High-quality, rotating electrical contacts are preferred for transmitting low-voltage signals, while both rolling brushes and knifes are suitable for making electrical contact with the pipe wall. Furthermore, temperature compensation is required for elimination of thermocouple signals.

The subject matter of the present invention is described with specificity to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the term "step" may be used herein to connote different elements of methods employed, the term should not be interpreted as implying any particular order among or between various steps herein disclosed unless and except when the order of individual steps is explicitly described. Alternative embodiments and implementations of the present invention will become apparent to those skilled in the art to which it pertains upon review of the specification, including the drawing figures.

The invention claimed is:

1. A system for measuring a voltage differential in a current-carrying pipe using a propulsion vehicle for conveying the system inside the pipe, the system comprising:
   a first contact for maintaining electrical contact with the pipe as the vehicle moves through the pipe;
   a second contact positioned in a spaced apart relationship from said first contact for maintaining electrical contact with the pipe as the vehicle moves through the pipe; and
   a voltage reading device connected to said first contact and said second contact for measuring the voltage between said first contact and said second contact as the vehicle moves through the pipe, wherein the voltage error is reduced to a microvolt range.

2. The system of claim 1 wherein said propulsion vehicle is a pig.

3. The system of claim 1 wherein said first contact comprises at least one of a plurality of brushes and knives.

4. The system of claim 1 wherein said first contact comprises at least one brush.

5. The system of claim 1 wherein said first contact comprises at least one knife.

6. The system of claim 1, wherein the first contact comprises at least one rotating brush.

7. The system of claim 1, wherein the first contact comprises a plurality of rotating brushes.

8. The system of claim 1, wherein the first contact and the second contact comprise at least one rotating brush.

9. The system of claim 1 wherein said first contact comprises one more devices for maintaining electrical contact between said pipe and said first contact.

10. The system of claim 9 wherein at least one of said devices is a brush.

11. The system of claim 9 wherein at least one of said devices is a knife.

12. The system of claim 9 wherein at least one of said devices is configured to reduce noise received by said voltage reading device.

13. The system of claim 9 wherein said second contact comprises one or more devices for maintaining electrical contact between said pipe and said second contact.

14. The system of claim 1 further comprising one or more electromechanical devices connected to said first contact for reducing noise received by said voltage reading device.

15. The system of claim 14 wherein said electromechanical device is a mercury contact.

16. The system of claim 14 wherein said electromechanical device is a slip ring contact.

17. The system of claim 1 further comprising means for compensating for thermocouple voltages.

18. The system of claim 17 wherein said means comprise a determination of bulk fluid reference voltages.

19. The system of claim 1 further comprising means for compensating for no contact events.

20. The system of claim 19 wherein said means comprise an alternating current pilot signal.

21. The system of claim 1 further comprising a location device for determining the position of said vehicle in the pipe.

22. The system of claim 21 wherein said location device is an odometer.

23. A method for measuring a voltage differential in a current-carrying pipe, the method comprising:
   inserting a propulsion vehicle into said pipe;
   utilizing a first contact positioned on said propulsion vehicle to maintain electrical contact with the pipe as the vehicle moves through the pipe;
   utilizing a second contact positioned in a spaced apart relationship from said first contact on said propulsion vehicle to maintain electrical contact with the pipe as the vehicle moves through the pipe;
   determining the voltage between said first contact and said second contact as the vehicle moves through the pipe, wherein the voltage error is reduced to a microvolt range.

24. The method of claim 23 wherein said propulsion vehicle is a pig.

25. The method of claim 23 wherein said first contact comprises at least one of a plurality of brushes and knives.

26. The method of claim 23, wherein the first contact comprises at least one rotating brush.

27. The method of claim 23, wherein the first contact comprises a plurality of rotating brushes.

28. The method of claim 23, wherein the first contact and the second contact comprise at least one rotating brush.

29. The method of claim 23 wherein said first contact comprises one more devices for maintaining electrical contact between said pipe and said first contact.

30. The method of claim 29 wherein at least one of said devices is a brush.

31. The method of claim 29 wherein at least one of said devices is a knife.

32. The method of claim 29 wherein at least one of said devices is configured to reduce noise in a voltage signal.

33. The method of claim 23 further comprising utilizing one or more electromechanical devices connected to said first contact to reduce noise in a voltage signal.

34. The method of claim 33 wherein said electromechanical device is a mercury contact.

35. The method of claim 33 wherein said electromechanical device is a slip ring contact.

36. The method of claim 23 further comprising compensating for thermocouple voltages.

37. The method of claim 36 wherein said compensation comprises a determination of a bulk fluid reference voltage.

38. The method of claim 23 further comprising compensating for no contact events.

39. The method of claim 38 wherein said compensation comprises utilizing an alternating current pilot signal to identify said no contact events.

40. The method of claim 23 further comprising determining the position of the vehicle in the pipe.

41. The method of claim 40 wherein determining the position of the vehicle in the pipe utilizes an odometer.

42. The method of claim 40 further comprising outputting voltage and position data.

43. The method of claim 40 wherein the position of the vehicle in the pipe is tracked in real time.

44. The method of claim 43 wherein said tracking utilizes a satellite and/or acoustic device.

45. A system for measuring a voltage differential a current-carrying pipe using a propulsion vehicle for conveying the system inside the pipe, the system comprising:

a first contact for maintaining electrical contact with the pipe as the vehicle moves through the pipe, wherein said first contact comprises at least one of a plurality of brushes and knives;

a second contact positioned in a spaced apart relationship from said first contact for maintaining electrical contact with the pipe as the vehicle moves through the pipe, wherein said second contact comprises at least one of a plurality of brushes and knives; and a voltage reading device connected to said first contact and said second contact for measuring the voltage between said first contact and said second contact as the vehicle moves through the pipe, wherein the voltage error is reduced to a microvolt range.

46. The system of claim 45, wherein the first contact comprises at least one rotating brush.

47. The system of claim 45, wherein the first contact comprises a plurality of rotating brushes.

48. The system of claim 45, wherein the first contact and the second contact comprise at least one rotating brush.

* * * * *